(12) United States Patent
Ellegaard et al.

(10) Patent No.: US 10,330,660 B2
(45) Date of Patent: Jun. 25, 2019

(54) WIRELESS SUBTERRANEAN SOIL MONITORING SYSTEM

(71) Applicant: AquaSpy, Inc., San Diego, CA (US)

(72) Inventors: Peter Ellegaard, San Diego, CA (US); Erkka Sointula, Salo (FI)

(73) Assignee: AQUASPY, INC., San Diego, CA (US)

( * ) Notice: Subject to any disclaimer, the term of this patent is extended or adjusted under 35 U.S.C. 154(b) by 50 days.

(21) Appl. No.: 15/215,536

(22) Filed: Jul. 20, 2016

(65) Prior Publication Data

US 2017/0023541 A1    Jan. 26, 2017

Related U.S. Application Data

(60) Provisional application No. 62/194,762, filed on Jul. 20, 2015.

(51) Int. Cl.
| | |
|---|---|
| *H04L 7/00* | (2006.01) |
| *H04Q 9/04* | (2006.01) |
| *A01G 25/16* | (2006.01) |
| *G01N 33/24* | (2006.01) |

(52) U.S. Cl.
CPC ......... *G01N 33/246* (2013.01); *A01G 25/167* (2013.01); *H04L 7/0079* (2013.01); *H04Q 9/04* (2013.01); *H04Q 2209/40* (2013.01); *H04Q 2209/845* (2013.01); *H04Q 2209/886* (2013.01)

(58) Field of Classification Search
CPC ..................................... G01N 33/246
See application file for complete search history.

(56) References Cited

U.S. PATENT DOCUMENTS

2014/0077969 A1*  3/2014  Vian ........................ H04Q 9/00
                                                          340/870.02

\* cited by examiner

*Primary Examiner* — Manuel A Rivera Vargas
(74) *Attorney, Agent, or Firm* — Steins & Associates, P.C.

(57) ABSTRACT

A Wireless Subterranean Soil Monitoring System. The system measures the complex permittivity around a subterranean antenna, and then responsively adjusts the antenna's tuning circuit according to the measured permittivity. Once tuned, the system will then execute the transmission of the probe data. Furthermore, the antenna design is adapted for subterranean use to further reduce the de-tuning effect of the adjacent soil.

10 Claims, 6 Drawing Sheets

WIRELESS SUBTERRANEAN SOIL MONITORING SYSTEM

This application is filed within one year of, and claims priority to Provisional Application Ser. No. 62/194,762, filed Jul. 20, 2015.

BACKGROUND OF THE INVENTION

1. Field of the Invention

This invention relates generally to agricultural automation systems and, more specifically, to a Wireless Subterranean Soil Monitoring System.

2. Description of Related Art

The monitoring of the moisture of soil for the purpose of optimizing the growth of crops has become increasingly important today, particularly in the environment of large, corporate farming operations. There are two common practices associated with the installation of soil moisture probes in the soil. The most prevalent method involves the installation of a soil monitoring probe in the ground once the plant emerges after planting (actually a series of probes to cover an entire planted field). Each probe is then connected to a telemetry system that provides power and receives the measured data from the probe. The telemetry will regularly upload the received data to a central database using cellular or other wireless technology. Typically, the telemetry system is located in close proximity to the probe—somewhere in the actual field of crops. Before the crop is harvested the system (probes and telemetry equipment) is extracted and removed from the field. These annual installation and extraction operations are costly and further only permits the grower to obtain data during a portion of the year (just after planting until just before harvesting).

A less common practice is to install the probe(s) in the soil and then trench the connecting cable to the perimeter of the field (typically about 100 meters away). This will allow the probe to reside in the field continuously for several years, providing data to the grower over the entire year. There are several drawbacks with the trenching method. First, it is a cumbersome and expensive exercise to trench the cable (to each probe). Second, there are several cases where normal field operations will result in one or more of the cables being severed, thereby breaking the connection to the probe.

What is needed is a system and method that permits the probe to reside continuously in the field without the need for expensive trenching, and without the risk of damage to the equipment due to normal field operations. It is believed that a wireless probe transmission system that is buried in close proximity to each probe, is the solution to this problem.

SUMMARY OF THE INVENTION

In light of the aforementioned problems associated with the prior systems and methods, it is an object of the present invention to provide a Wireless Subterranean Soil Monitoring System. The system should measure the complex permittivity around a subterranean antenna, and then responsively adjust the antenna's tuning circuit according to the measured permittivity. Once tuned, the system should then execute the transmission of the probe data. Furthermore, the antenna structural design should be adapted for subterranean use to further reduce the de-tuning effect of the adjacent soil.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

DETAILED DESCRIPTION OF THE PREFERRED EMBODIMENTS

The following description is provided to enable any person skilled in the art to make and use the invention and sets forth the best modes contemplated by the inventors of carrying out his/their invention. Various modifications, however, will remain readily apparent to those skilled in the art, since the generic principles of the present invention have been defined herein specifically to provide a Wireless Subterranean Soil Monitoring System.

This invention describes a system that can reside next to the probe in the field, buried at any depth. It contains a battery pack, interface to the probe, a temporary data storage and a wireless transceiver. The invention solves the problem of being able to transmit and receive data via an antenna that is subject to varying permittivity of the adjacent soil.

Any antenna that receives and transmits data must first be optimized to maximum efficiency in its typical environment. In the case where the antenna is buried in soil, the antenna efficiency will significantly degrade as the soil changes its complex permittivity due to the commonly-occurring changes in water and fertilizer content (in the soil).

Figure 1:
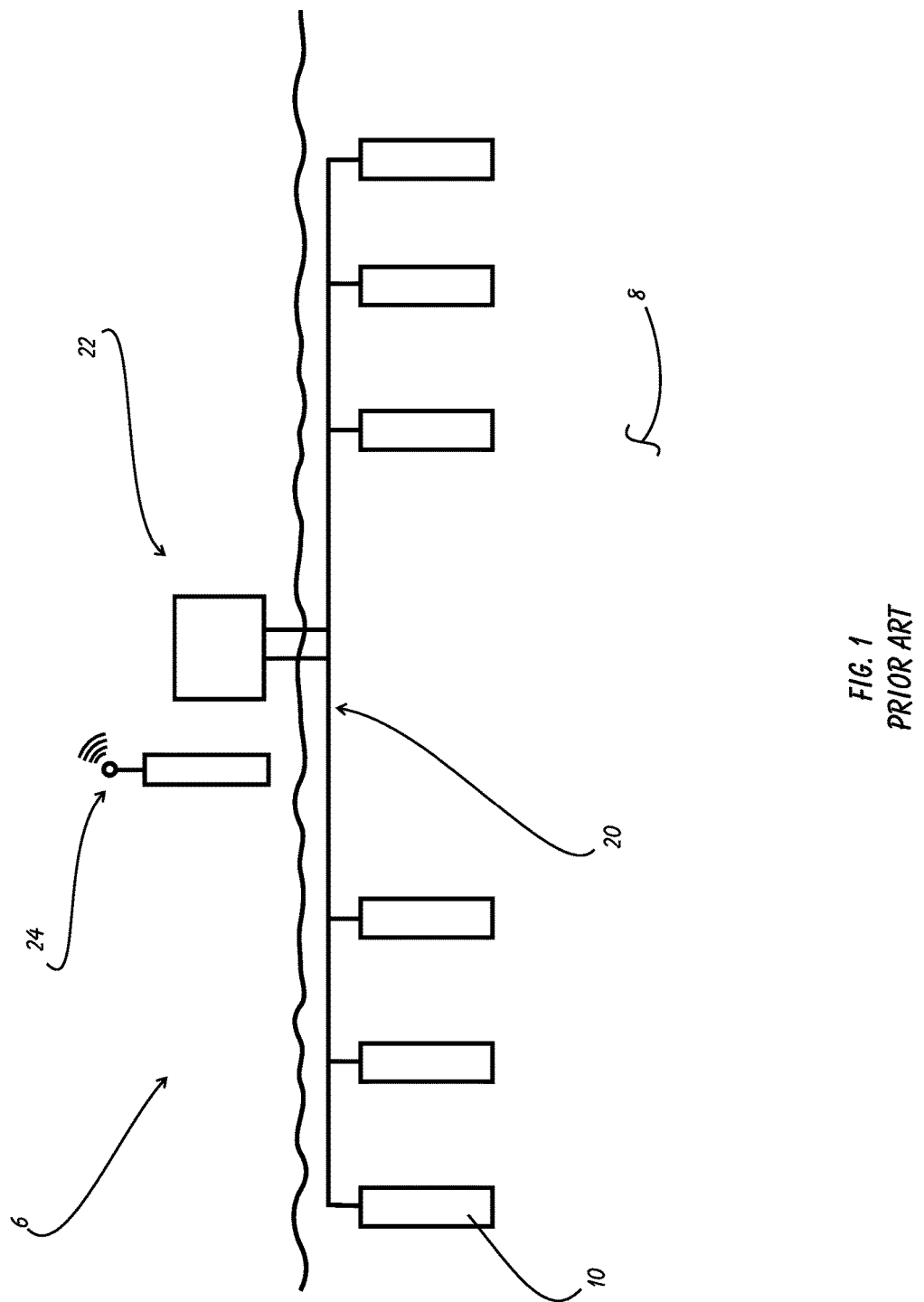
FIG. 1 is a cutaway side view a conventional soil moisture monitoring network.

The present invention can best be understood by initial consideration of FIG. 1.[1] FIG. 1 is a cutaway side view a conventional soil moisture monitoring network 6. As discussed previously, there are a series of soil moisture probes 10 buried in the soil 8 around the planted area. The probes 10 are individually connected to the probe controller/transmitter 22 by control conduits 20 (buried cables). The difference between the two most prevalent prior systems is the depth at which the conduits 20 are buried.

[1] As used throughout this disclosure, element numbers enclosed in square brackets [ ] indicates that the referenced element is not shown in the instant drawing figure, but rather is displayed elsewhere in another drawing figure.

In normal operation, the controller/transmitter 22 will poll each probe 10 on a regular periodicity to obtain the moisture readings of the soil 8 adjacent to each probe 10. The probes 10 are aligned horizontally, and provide distinct moisture readings at depths along the length of each probe 10. On a regular basis (or when requested), the controller/transmitter 22 will transmit the moisture data to a centralized data repository by an attached external communications tower 24. As discussed above, the transmission is wireless by either cellular or some other approach. The probe controller/transmitter typically has an internal power supply (e.g. a battery), and may be equipped with a solar panel to recharge the onboard battery pack for prolonged, continuous use.

Figure 2:
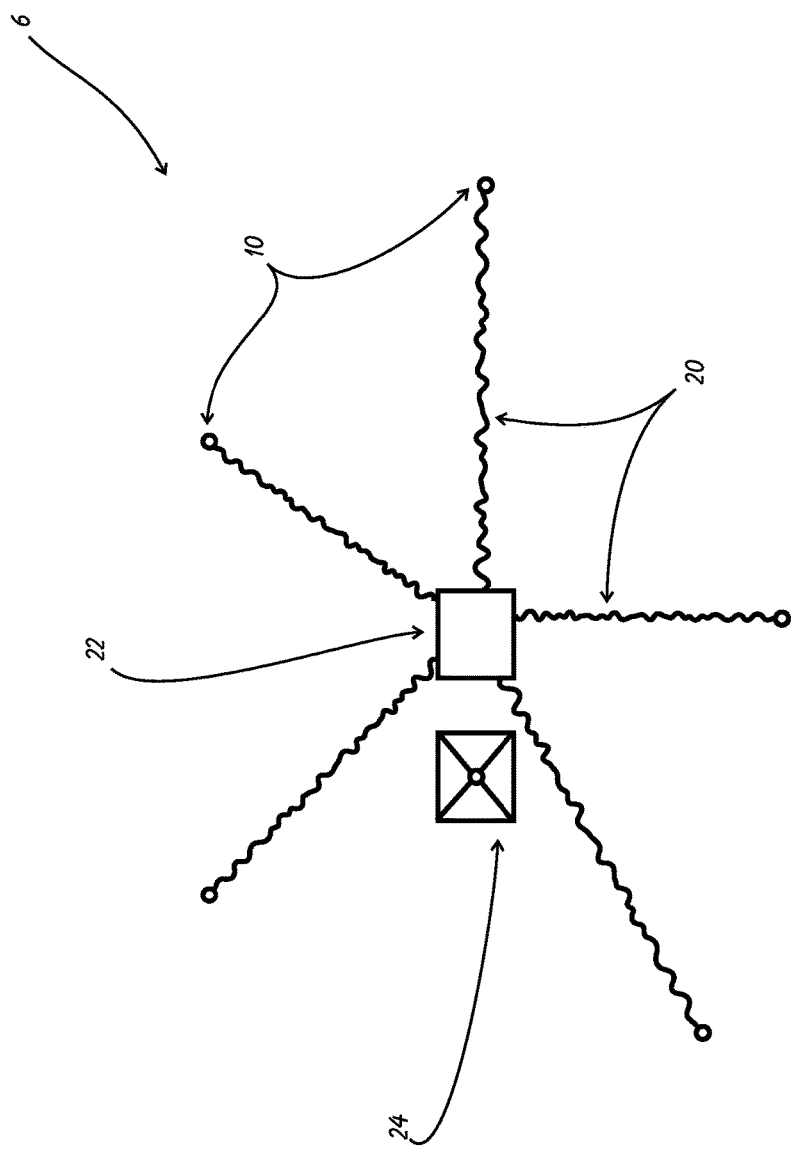
FIG. 2 is a top view of the network of FIG. 1.

FIG. 2 is a top view of the network 6 of FIG. 1. As seen here, the conduits 20 traverse the planted field (this would be the non-trenched approach). It is clear from this view that any attempt at tilling or otherwise operating heavy equipment in the field is guaranteed to impact the crisscrossing cables (conduits 20). It is this problem that is solved by the present invention, first introduced in FIG. 3.

Figure 3:
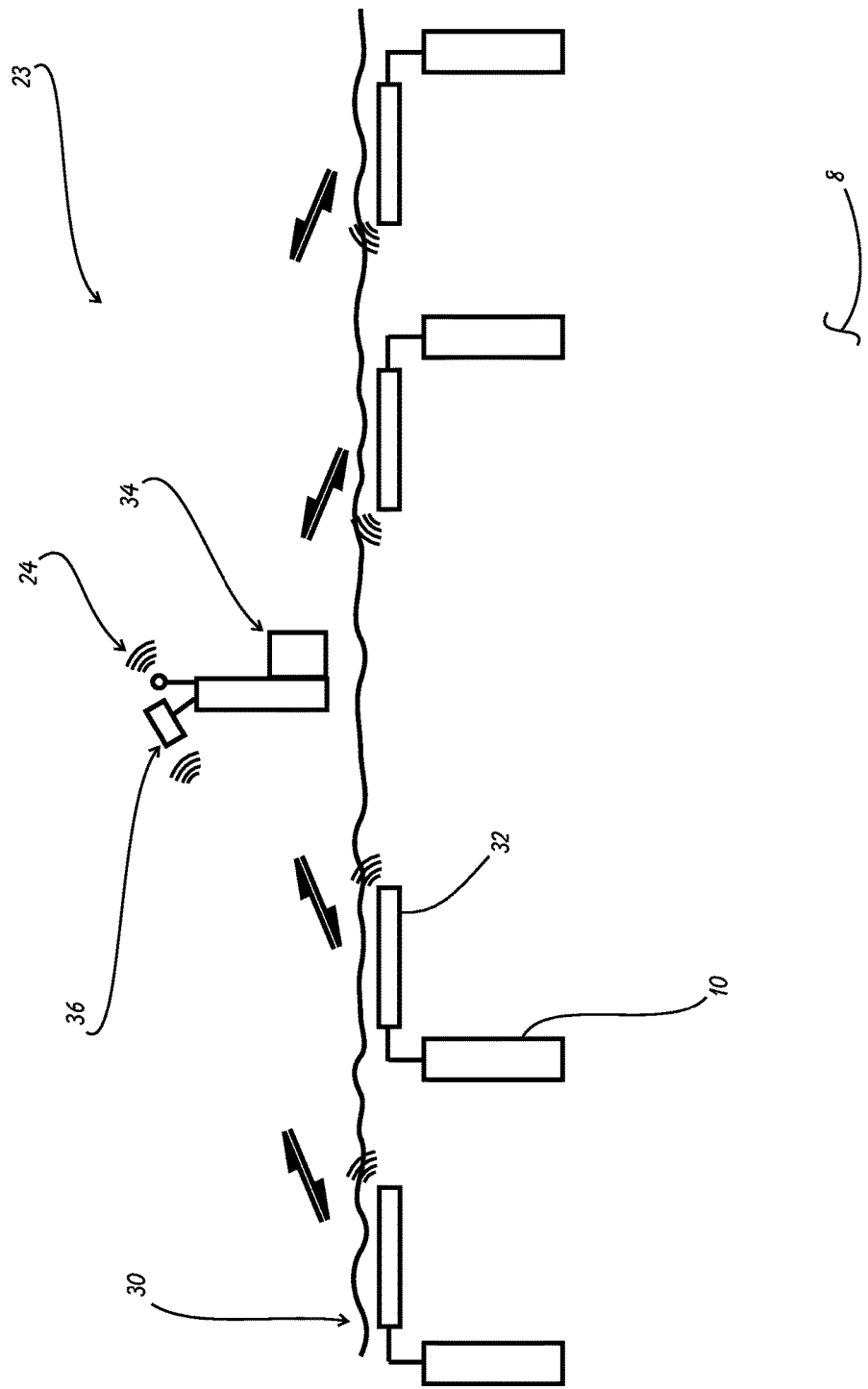
FIG. 3 is a cutaway side view of a preferred embodiment of the wireless soil moisture monitoring network of the present invention.

FIG. 3 is a cutaway side view of a preferred embodiment of the wireless soil moisture monitoring network 23 of the present invention. The network 23 is comprised of one or more subterranean sensor/transmitter assemblies 30. Each sensor/transmitter assembly 30 has a soil moisture probe 10 interconnected with a subterranean transmitter 32. The sensor'/transmitter assemblies 30 communicate wirelessly with the probe communications tower 36.

The probe network controller/receiver/transmitter (PNCRT) 34 does double-duty—it handles the conventional communications with the central data repository, to transmit the soil moisture data by cellular or other wireless means via the external communications tower 24. It further handles the wireless communications with the individual sensor/transmitter assemblies 30. Like the probe controller/transmitter of the prior system, the PNCRT 34 also will have an onboard power supply (typically a battery), and usually will have a solar panel to keep the onboard battery fully charged.

As should be apparent from this drawing figure, there are no longer cables interconnecting the central probe control system and the individual probes 10. Consequently, the expense and damage risk presented by the crisscrossing control conduits [20] has been eliminated. One note regarding the identification of the probe communications tower 36 and the external communications tower 24 - these are identified as separate entities for the purpose of explanation only. It is possible that only a single tower is employed, depending upon a number of factors, including location, installation requirements, and wireless communication technology, among others. If we now turn to FIG. 4, we can examine the features of this new probe assembly.

Figure 4:
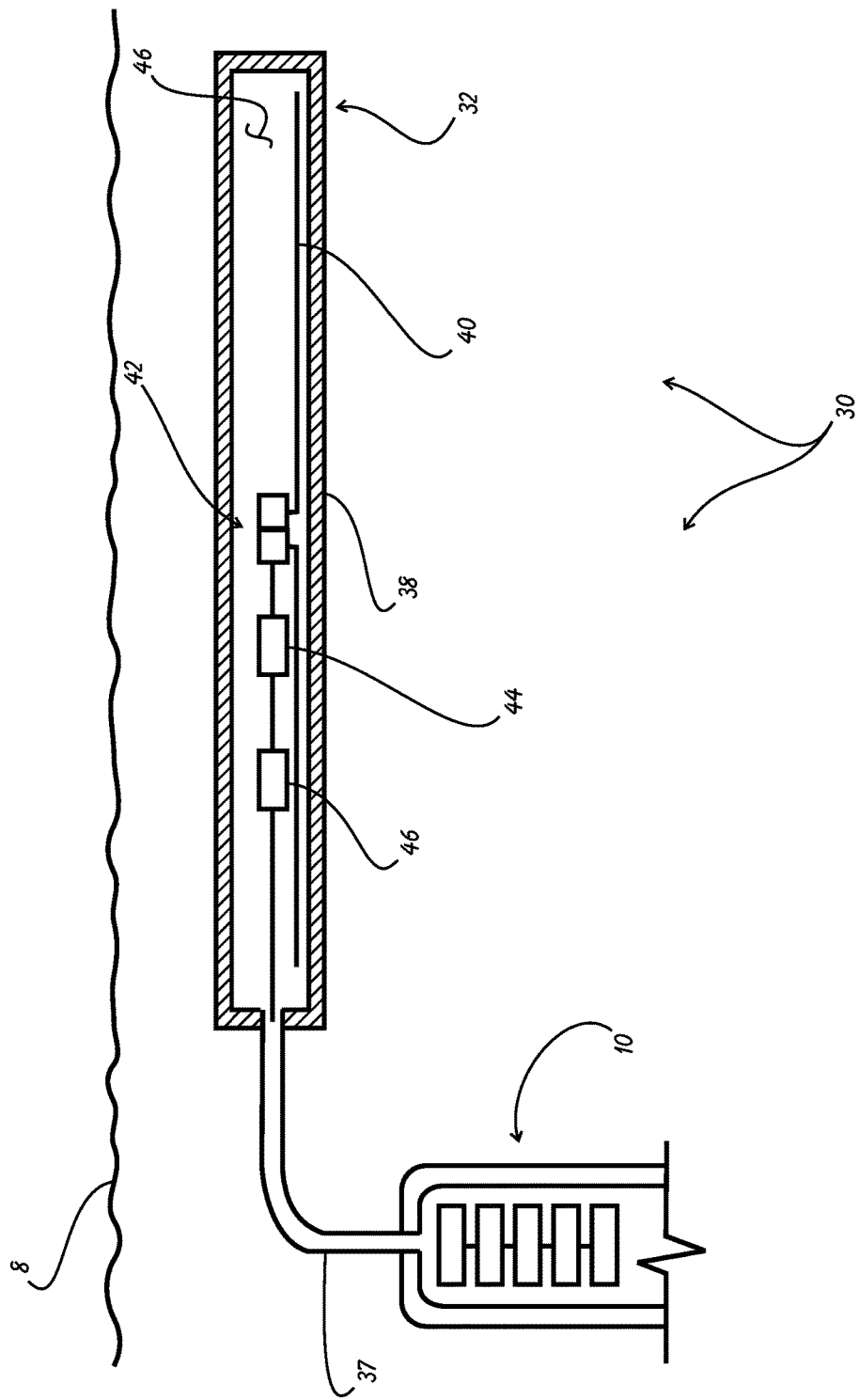
FIG. 4 is a partial cutaway side view of the subterranean sensor/transmitter assembly of the network of FIG. 3.

FIG. 4 is a partial cutaway side view of the subterranean sensor/transmitter assembly 30 of the network [23] of FIG. 3. There are two main components to the assembly 30: the soil moisture probe 10, and the subterranean transmitter 32. The probe 10 could be any suitable soil moisture probe, but would preferably be of the type discussed in a companion patent application entitled "Soil Moisture and Electrical Conductivity Probe." There is a short local control conduit (cable) 37 interconnecting the probe 10 and the transmitter 32, but this is expected to be very short, and to be completely buried under the soil 8, at or below the level of the transmitter 32.

The transmitter 32 is typically a hollow, elongate tube that is sealed at both ends. Conventional 2-inch diameter PVC pipe has proven to be very suitable, but other materials could also be used. The key is that the walls of the housing 38 be long-lasting for prolonged underground stays, while also being "transparent" to the wireless transmissions between the transmitter 32 and the PNCRT [34]. A prototype transmitter 32 has functioned very well with a housing 38 that is 8 (eight) feet in length.

The basic components of the transmitter 32 are a basic dipole antenna 40 extending outwardly to the opposing ends of the housing 38. A probe local controller 44 controls the operation of the transmitter 32, as well as the operation of the soil moisture probe 10. There is a transceiver/tuner 42 within the housing 38 for communicating with the PNCRT [34], and a battery 46 to supply sufficient power to operate all of the components of the assembly 30 for at least a year.

It has been proven that a low power, low frequency transmitter can be operated for at least one year on a readily-available battery 46 with the distance between the PNCRT [34] and the probes 10 being up to one mile.

The interior of the housing 38 may be filled with air (or other gas), or it may be filled with foam (e.g. chemically-expanding foam). While air or other gas will provide the least barrier to wireless transmissions from the antenna 40, it provides no structural rigidity. The benefit of foam 46 is that it provides substantial structural rigidity, while also water-proofing the internal components (and making them tamper-proof). This while also presenting a very small additional barrier to wireless transmissions.

Figure 5:
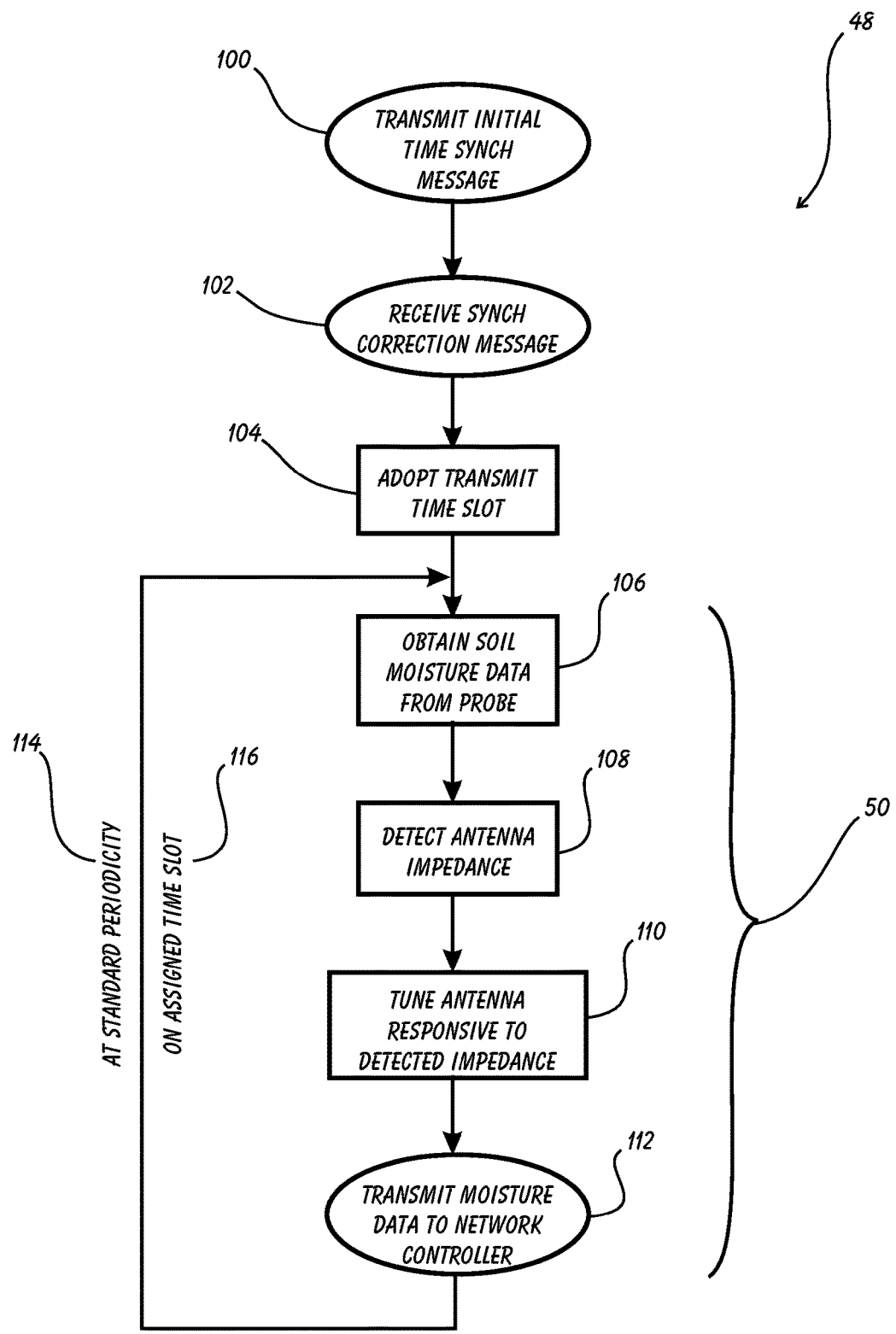
FIG. 5 is a flowchart depicting the transmission method of probes within the network of FIG. 3.
Figure 6:
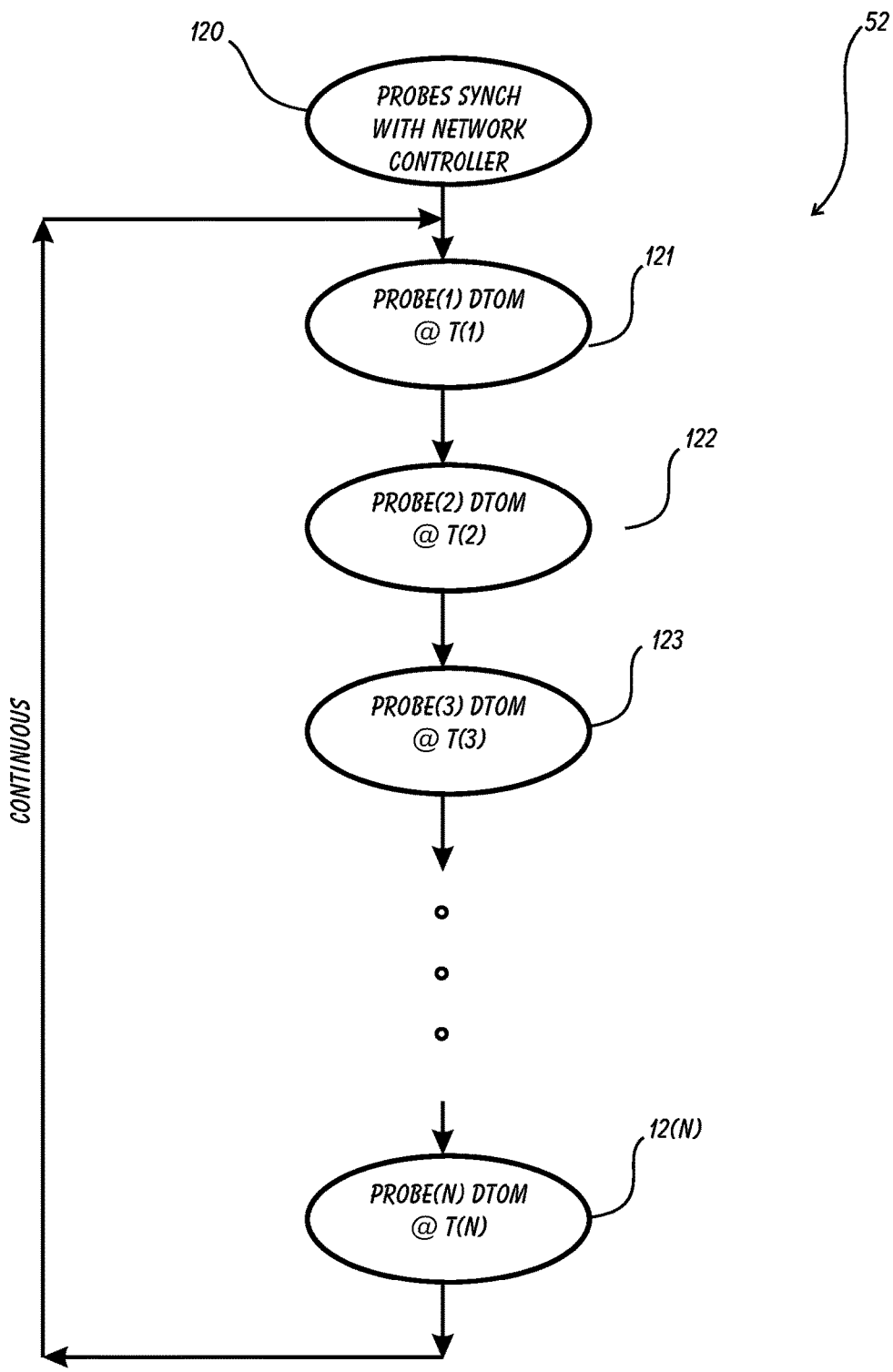
FIG. 6 is a flowchart of the communications method of the network of FIG. 3.

Having introduced the physical components of the device and system of the present invention, we will now examine the novel operational features necessary for the system to function effectively. FIGS. 5 and 6 depict these features.

FIG. 5 is a flowchart depicting the transmission method 48 for probes within the network of FIG. 3. There are a few key aspects to the successful operation of the wireless equipment previously described above: (1) the wireless probe transmitters must be capable of making their transmissions from underground; (2) that the antennas within the probe transmitters are equipped to adjust/tune the transmission characteristics in response to the changing permittivity characteristics of the soil surrounding the antenna housing; (3) that the network of several sensor/transmitter assemblies are capable of cooperating with one another in communicating with a single PNCRT; and (4) that all of these functions are carried out using very low power demand so that the sensor/transmitter assemblies can remain buried for a year or more without the need for a very expensive battery.

To that end the method 48 (which is focused on a single probe/transmitter assembly) commences with the assembly [30] transmitting an initial time synchronization message to the PNCRT [34] 100. The PNCRT [34] identifies the assembly [30], and returns a message that corrects any discrepancy between the internal time on the assembly [30], and that of the PNCRT [34], that is received by the assembly [30] and applied so that the assembly [30] has an internal clock that is correlated with the master clock in the PNCRT [34].

The receipt of this message will also cause the assembly [30] to adopt a time slot 104. This means that for a particular transmission periodicity, this assembly [30] will always transmit at a pre-assigned time slot. This allows for several assemblies [30] within the same network [23] to proceed through a "round robin" set of sequential transmissions. This eliminates the need for handshakes between each assembly [30] and the PNCRT [34] (since the individual transmissions are one-directional), which simplifies the equipment design and reduces the power demand (thereby prolonging battery life).

The assembly [30] will, just before transmitting data, will obtain a set of soil moisture data from its probe [10] 106.

The assembly [30] will then, utilizing the antenna itself as a field sensor, detect the complex impedance of the antenna 108. This just-detected complex impedance information will be used by the assembly [30] to tune the antenna characteristics 110 so that the transmission power is optimized (and electrical demand is reduced).

Only then will the assembly [30] make its transmission to the PNCRT [34] 112.

Going forward, the assembly [30] will continue to loop at its assigned time slot 116, within the established periodicity for the network 114, to repeat steps 106-112. This loop of steps is referred to collectively as the probe data transmission and optimization method 50 (within the entire transmission method 48).

FIG. 6 illuminates the application of the method of FIG. 5, as it is applied to a network of assemblies [30]. First, all of the probe assemblies [30] conduct their synchronization with the PNCRT [34] 120, and then the individual assemblies [30] sequentially execute the Data Transmission and Optimization Method [50] 121, etc. for "N" assemblies [30] that are members of the network [23]. This will continue to loop continuously until batteries expire or the network [23] is shut down for another reasons.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method for remote measurement of soil moisture content, comprising the steps of:
    first transmitting a wireless time synchronization message said transmitting performed by a first subterranean sensor-transmitter assembly;
    receiving said time synchronization message said receiving performed by a central receiver-controller-transmitter assembly;
    determining a time correction responsive to the content of said time synchronization message said determining performed by said central receiver-controller-transmitter assembly;
    second transmitting a synchronization correction message responsive to said time correction, said synchronization correction message transmitting performed by said central receiver-controller-transmitter assembly;
    tuning an antenna element in said first subterranean sensor-transmitter assembly responsive to soil moisture content adjacent to said first subterranean sensor-transmitter assembly said antenna element tuning step responsive to said first and second transmitting and said receiving and determining steps in order to improve reliability and performance of said antenna element and to further reduce power demand by said first subterranean sensor-transmitter assembly to an optimum level;
    determining soil moisture content at incremental depths of said soil with said first subterranean sensor-transmitter assembly; and
    wirelessly transmitting said soil moisture content of said second determining by said first subterranean sensor-transmitter assembly responsive to said tuning.

2. The method for measuring soil moisture content of claim 1, further comprising the steps of:
    transmitting a wireless time synchronization message, said time synchronization transmitting performed by a second subterranean sensor-transmitter assembly;
    receiving said time synchronization message, said time synchronization message receiving performed by said central receiver-controller-transmitter assembly;
    determining a time correction responsive to the content of said time synchronization message, said time correction determining performed by said central receiver-controller-transmitter assembly;
    second transmitting a synchronization correction message responsive to said time correction, said second transmitting performed by said central receiver-controller-transmitter assembly, said synchronization correction message of said second transmitting further comprising a time slot assignment;
    tuning an antenna element in said second subterranean sensor-transmitter assembly responsive to soil moisture content adjacent to said second subterranean sensor-transmitter assembly;
    determining soil moisture content at incremental depths of said soil with said second subterranean sensor-transmitter assembly; and
    wirelessly transmitting said soil moisture content of said second determining by said second subterranean sensor-transmitter assembly responsive to said second subterranean sensor-transmitter tuning and said time slot assignment.

3. The method of measuring soil moisture content of claim 2, wherein said tuning steps comprises detecting the impedance of an antenna element in each said subterranean sensor-transmitter assembly, and tuning transmission properties of each said subterranean sensor-transmitter assembly responsively thereto.

4. The method of measuring soil moisture content of claim 2, wherein said wireless transmitting steps are executed by said subterranean sensor-transmitter assemblies responsive to the contents of said synchronization correction messages during each said subterranean sensor-transmitter assembly's said time slot assignment.

5. The method of measuring soil moisture content of claim 1, wherein said tuning step comprises detecting the impedance of an antenna element in said subterranean sensor-transmitter assembly, and tuning the transmission properties of said subterranean sensor-transmitter assembly responsively thereto.

6. The method of measuring soil moisture content of claim 1, wherein said wireless transmitting step is executed by said subterranean sensor-transmitter assembly responsive to the contents of said synchronization correction message.

7. A wireless soil moisture monitoring network, comprising:
    a central communications tower having a wireless communications antenna means; and
    at least one subterranean sensor-transmitter assembly in communication with said central communications tower, said sensor-transmitter assembly comprising:
        a soil moisture measuring assembly; and
        a subterranean transmitter assembly in communication with said soil moisture measuring assembly and said central communications tower, said subterranean transmitter assembly comprising:
            an antenna element; and
            a transceiver-tuner system configured to determine the antenna impedance characteristics of said antenna element and responsively configuring wireless transmission parameters of said transceiver-tuner system, whereby said transceiver-tuner system requires the lowest power demand possible and said transceiver-tuner system reliability and performance is optimized.

8. The wireless soil moisture monitoring network of claim 7, wherein said subterranean transmitter assembly comprises a housing encasing said antenna element and said transceiver-tuner system, said housing substantially filled with closed cell foam insulation.

9. A wireless moisture monitoring assembly for transmitting messages containing data responsive to the moisture level of a volume of soil, comprising:
    a soil moisture probe installed in said soil volume configured to estimate moisture content within said soil volume;

a subterranean transmitter installed in said soil volume and in communication with said soil moisture probe via a local control conduit, said subterranean transmitter comprising:

a housing;

an antenna within said housing; and a tuner assembly within said housing, said tuner configured to optimize wireless transmission parameters for said antenna responsive to the moisture level surrounding said transmitter housing.

10. The wireless moisture monitoring assembly of claim 9, wherein said housing is substantially filled with closed cell foam insulation material.

\* \* \* \* \*